United States Patent [19]

Vicari et al.

[11] Patent Number: 5,072,025
[45] Date of Patent: * Dec. 10, 1991

[54] PROCESS FOR THE PRODUCTION OF 3,5-DISUBSTITUTED-4-ACETOXYSTYRENE

[75] Inventors: Richard Vicari, Chatham Township, Morris County, N.J.; Mohammad Aslam, Corpus Christi, Tex.; Wilson B. Ray, Beeville, Tex.; Kenneth G. Davenport, Hofheim, Fed. Rep. of Germany; Ralph Dammel, Mainz-Bretzenheim, Fed. Rep. of Germany; Juergen Lingnau, Mainz-Laubenheim, Fed. Rep. of Germany; Karl-Friedrich Doessel, Wiesbaden, Fed. Rep. of Germany

[73] Assignee: Hoechst Celanese Corporation, Somerville, N.J.

[*] Notice: The portion of the term of this patent subsequent to Oct. 23, 2007 has been disclaimed.

[21] Appl. No.: 559,759

[22] Filed: Jul. 26, 1990

Related U.S. Application Data

[60] Division of Ser. No. 226,260, Aug. 2, 1988, Pat. No. 4,965,400, which is a continuation-in-part of Ser. No. 97,809, Sep. 16, 1987, abandoned.

[51] Int. Cl.$^5$ .............................................. C07C 67/00
[52] U.S. Cl. .................................... 560/130; 560/142; 560/231; 560/239; 560/250; 560/251; 560/252; 560/254; 568/337
[58] Field of Search ................ 560/130, 142, 231, 239, 560/250, 251, 252, 254

[56] References Cited

U.S. PATENT DOCUMENTS

| | | | |
|---|---|---|---|
| 2,276,138 | 3/1942 | Alderman et al. | 560/254 |
| 2,687,422 | 8/1954 | Overberger | 260/410.5 |
| 3,624,134 | 11/1971 | Kablaoui | 560/254 |
| 3,970,534 | 7/1976 | Fujiwara et al. | 204/159.17 |
| 4,451,676 | 5/1984 | Everly | 568/780 |
| 4,927,956 | 5/1990 | Vicari et al. | 560/130 |
| 4,965,400 | 10/1990 | Vicari et al. | 560/130 |

Primary Examiner—Jose G. Dees
Assistant Examiner—Vera C. Clarke
Attorney, Agent, or Firm—Donald R. Cassady; Shirley L. Church; Rich Roberts

[57] ABSTRACT

3-substituted-4-hydroxy- and 4-acetoxystyrene compounds, especially 3,5-di(methyl, bromo or chloro)-4-acetoxystyrene as well as a process for its preparation. 2,6-dimethylphenol is acylated with acetic anhydride and HF catalyzed to produce 3,5-dimethyl-4-hydroxyacetophenone. After subsequent esterification with acetic anhydride and catalyzed hydrogenation to form 1-(3′,5′-dimethyl-4′-acetoxyphenyl)ethanol, this intermediate is then dehydrated with an acid and a polymerization inhibitor to produce 3,5-dimethyl-4-acetoxystyrene.

4 Claims, No Drawings

PROCESS FOR THE PRODUCTION OF 3,5-DISUBSTITUTED-4-ACETOXYSTYRENE

This application is a divisional application of pending U.S. patent application Ser. No. 07/226,260, filed Aug. 2, 1988, now U.S. Pat. No. 4,965,400, which is a continuation-in-part of U.S. patent application Ser. No. 07/097,809, filed Sept. 16, 1987, now abandoned.

BACKGROUND OF THE INVENTION

The present invention relates to 3-substituted-4-hydroxy- and 4-acetoxystyrene compounds and more particularly to 3,5-disubstituted-4-acetoxystyrene wherein the 3,5-substitution is independently $C_1$ to $C_{10}$ alkyl or alkoxy, amino, such as primary or secondary amino or halo, and a process for its preparation. In its most preferred form, the invention relates to 3-mono- and 3,5-dihalogenated 4-acetoxystyrenes which contain chlorine or bromine as the halogen, and a method of preparation thereof.

3,5-dibromo-4-hydroxystyrene compounds have been known for a long time and were initially prepared from 4-hydroxycinnamic acid by a) bromination of positions 3 and 5 on the ring as well as addition of bromine to the double bond.

b) dehydrobromination with concurrent decarboxylation, leading to reconstitution of the vinylic double bond.

c) then, addition of hydrogen bromide to said double bond to form a saturated vicinal dibromide, d) finally, by debromination for reconstruction of the vinylic double bond (see Liebigs Annalen der Chemie, 322, 235 (1902)) as shown in the following scheme:

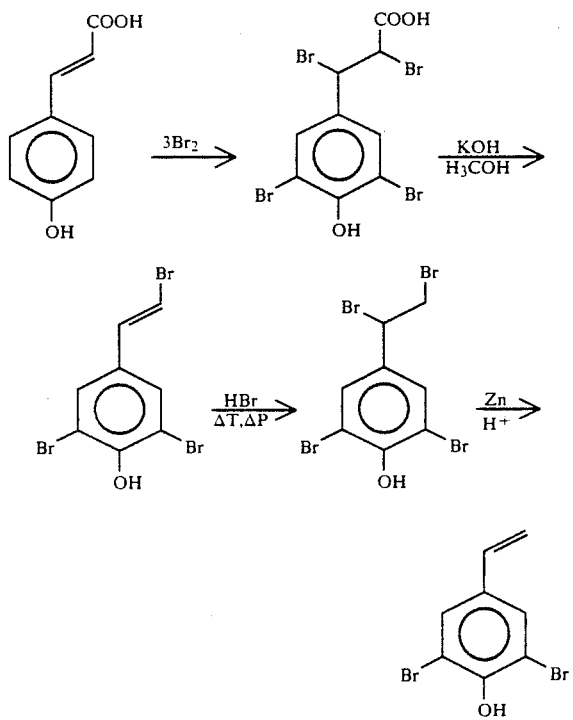

It is known in the art to produce monomers, homopolymers and copolymers of unsubstituted 4-acetoxystyrene and to hydrolyze the same to produce 4-hydroxystyrene derivatives or polyvinyl phenols. Such find use in the production of photoresists, adhesives, coating compositions, and the like. In particular, polymers or copolymers prepared from non-halogenated monomers are used for preparing coating compositions and as binders for photoresists. In this connection, reference is made to post-brominated poly(4-hydroxy)styrenes which are used in accordance with German patent application P 37 30 784.3 as radiation-sensitive compounds in corresponding photoresists. The compounds of this invention find use as intermediates in the production of such polymers as poly(3,5-dimethyl-4-acetoxystyrene) and poly(3,5-dimethyl-4-hydroxystyrene). These later compounds are useful as improved binder resins for photoresists which have a more advantageous dissolution rate in commercially accepted photoresist developers, and are more fully described in U.S. patent application Ser. No. 07/097815 filed on even date herewith and incorporated herein by reference, now abandoned. Alpha acetoxystyrene and beta acetoxystyrenes are described in U.S. Pat. No. 4,144,063 and acetoxymethylstyrene is taught in U.S. Pat. No. 3,963,495. U.S. Pat. No. 4,075,237 describes 1,4-dimethyl-2-hydroxystyrene, while U.S. Pat. No. 4,565,846 teaches the use of poly(3,5-dimethyl-4-hydroxystyrene). Japanese patent 84023747 describes anti-static compounds employing poly-acetoxymethylstyrene and U.S. Pat. No. 4,221,700 describes a stabilized synthetic polymer composition using poly(alkylated alkenylphenol) including 2-methyl paravinyl phenol. U.S. Pat. Nos. 4,600,683 and 4,543,397 describe poly (alphamethyl vinylphenol). U.S. Pat. Nos. 4,517,028; 4,460,770 and 4,539,051 describe dimethyl vinyl phenol.

SUMMARY OF THE INVENTION

The invention provides as a novel compound, 3,5-disubstituted-4-acetoxystyrene.

The invention also provides a process for the production of 3,5-disubstituted-4-acetoxystyrene which comprises (a) acylating 2,6-disubstituted phenol, for example with acetic anhydride under suitable catalysis to provide 3,5-disubstituted-4-hydroxyacetophenone, then (b) esterifying the 3,5-disubstituted-4-hydroxyacetophenone to produce 3,5-disubstituted-4-acetoxyacetophenone, then (c) hydrogenating the 3,5-disubstituted-4-acetoxyacetophenone to form 1-(3',5'-disubstituted-4'-acetoxyphenyl)ethanol and then (d) dehydrating the 1-(3',5'-disubstituted-4'-acetoxyphenyl)ethanol to form 3,5 disubstituted-4-acetoxystyrene. Each of the above 3,5-substitutions are independently $C_1$ to $C_{10}$ alkyl or alkoxy, amino or halo. The invention further provides 3-substituted-4-hydroxy- and 4-acetoxystyrene compounds having the formula:

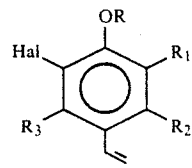

wherein:
R is hydrogen or acetyl; and
Hal is chlorine or bromine; and
R1, R2 and R3 are independently hydrogen, alkyl, alkoxy, or halogen; and
wherein R1 and R2 may combined to form a cycloaliphatic ring, consisting of 6 to 12 members; and wherein, when R is acetyl at least one of $R_1$, $R_2$ and $R_3$ and are not hydrogen, and when R is hydrogen, at least two of $R_1$, $R_2$ and $R_3$ are not hydrogen.

DETAILED DESCRIPTION OF THE PREFERRED EMBODIMENT

In the preferred embodiment, the preferred 3,5-substitution is methyl and the preferred embodiment will now be described in detail. The other substitutions are obtained analogously. In the process for the production of 3,5-dimethyl-4-acetoxystyrene, one begins with 2,6-dimethylphenol, which is readily commercially available, and esterifies it with acetic anhydride to produce 2,6-dimethyl-4-phenylacetate. Then, via a Friedel-Crafts catalysis or Fries rearrangement this is converted to 3,5-dimethyl-4-hydroxyacetophenone. This is then esterified with, for example, acetic anhydride to form 3,5-dimethyl-4-acetoxyacetophenone. The latter is then hydrogenated to form 1-(3',5'-dimethyl-4'-acetoxyphenyl)ethanol. This is then dehydrated with an acid to form 3,5-dimethyl-4-acetoxystyrene monomer.

A typical reaction sequence may be described schematically as follows:

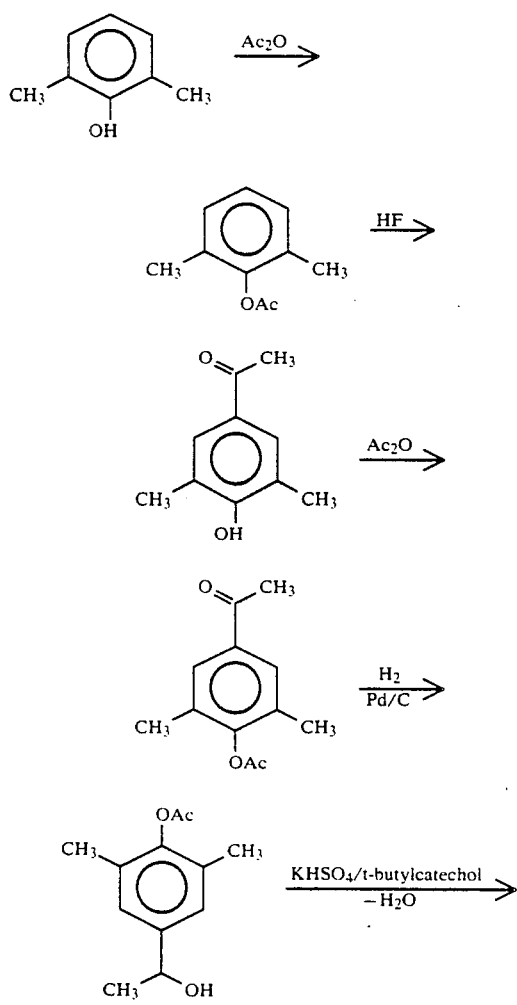

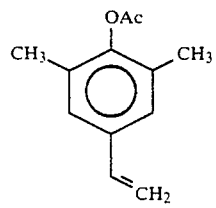

In the preferred embodiment the first two reaction steps proceed essentially simultaneously. That is, one charges the reaction vessel with 2,6-dimethylphenol, a slight excess of acetic anhydride and a Friedel-Crafts catalyst such as hydrogen fluoride. The acylation is conducted at a temperature of from about 5° C. to about 100° C., or more preferably from about 20° C. to about 80° C. A most preferred temperature is about 50° C. The reaction proceeds at a preferred pressure of from about 700 mm Hg to about 780 mm Hg for from about 1 to about 5 hours. Although hydrogen fluoride is the preferred catalyst, others may be also used such as $AlCl_3$, $H_2SO_4$, $BF_3$, and $SnCl_4$. In the alternative, the acylation may be conducted by a Fries rearrangement, in a manner well known to the skilled artisan. Attempts to directly reduce the keto functionality in 3,5-disubstituted 4-hydroxyacetophenones by means of e.g. catalytic hydrogenation or complex hydrides, as known to the skilled artisan, invariably lead to overreduction with exclusive formation of 4-ethylphenol derivatives. While not wishing to be bound by theory it is believed that this behavior is caused by formation of quinonemethide intermediates which are then preferentially reduced at the methide carbon as shown in the following scheme:

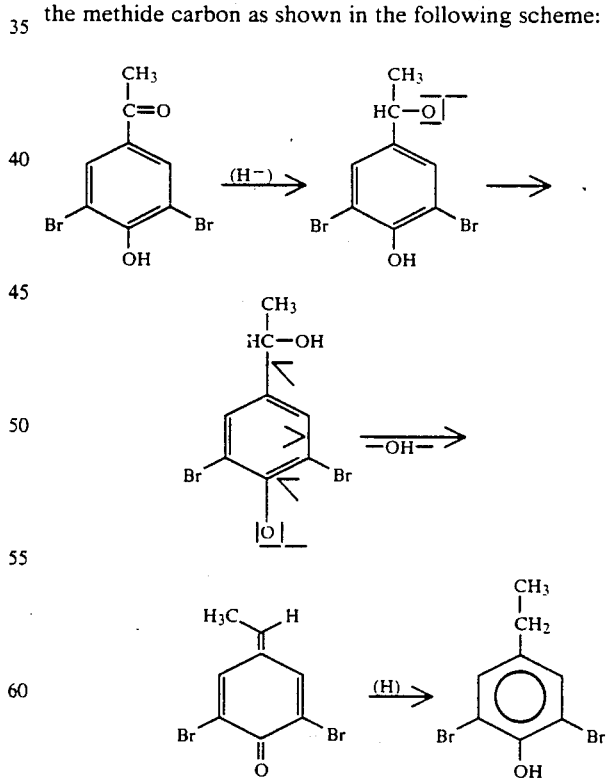

This undesirable behavior can be pre-empted by preventing phenolate ion formation, which is essential to the above mechanism. This is most easily done by protecting the phenolic functionality, e.g. by esterification.

Esterification of the hydroxyl group for its protection is preferably accomplished with acetyl chloride or with acetic anhydride. However, any reagents known to protect hydroxyl functions can be used. These include in particular the formation of ethers, such as methyl, methoxymethyl, 2-methoxyethoxymethyl, methylthiomethyl, tetrahydropyranyl, cyclopropylmethyl, allyl, isopropyl, cyclohexyl, t-butyl, benzyl, o-nitrobenzyl, 9-anthrylmethyl, and 4-picolyl ethers, but also silyl ethers, such as trimethylsilyl and t-butyldimethylsilyl ethers, esters such as acetates, pivaloates, benzoates, and 9-fluorene-carboxylates, carbonates such as methyl, 2,2,2-trichloroethyl, vinyl, and benzyl carbonates, arylcarbamates, and sulfonates such as methanesulfonates and toluenesulfonates. Protective groups of this type are described by Theodora W. Green, Protective Groups in Organic Synthesis, John Wiley & Sons, 1981. However, the acetoxy group is particularly preferred. The reaction product 3,5-dimethyl-4-hydroxyacetophenone is therefore esterified with a suitable acetylating agent, preferably with acetic anhydride. In this process, the 3,5-dimethyl-4-hydroxyacetophenone is refluxed with an excess of acetic anhydride for from about 15 to about 20 hours. Excess acetic anhydride as well as generated acetic acid are removed by distillation in vacuo. This is conducted, for example at a pressure of from about 15 to about 30 mm Hg and at a temperature of from about 15° C. to about 40° C., preferably from about 30° C. to about 35° C. The resultant 3,5-dimethyl-4-acetoxyacetophenone is then preferably flash distilled at a pressure of from about 10 to about 40 mm Hg and at a temperature of from about 105° C. to about 125° C. and the resultant product appears as a colorless liquid which solidifies at room temperature.

The 3,5-dimethyl-4-acetoxyacetophenone is then catalytically hydrogenated. The reduction of the ketone function can be done with complex hydrides and by catalytic reduction with hydrogen. Sodium borohydride is a preferred complex hydride. Lithium borohydride is also possible as well as reaction products that arise for example upon dissolution of sodium borohydride or lithium borohydride in alcohols. The preferred reaction medium in reduction with complex hydrides is ethanol or mixtures of organic solvents miscible with water, such as THF/water mixtures. In the preferred embodiment, an autoclave is first passivated, for example first with 30% $HNO_3$ and then with KOH/isopropanol. It is then charged with the 3,5-dimethyl-4-acetoxyacetophenone, an excess of hydrogen gas under pressure, a sufficient amount of a suitable catalyst to drive the reaction, and a suitable solvent. One preferred catalyst is Pd/C in an amount of from about 1 to about 4 percent by weight of the 3,5-dimethyl-4-acetoxyacetophenone. Other suitable catalysts non-exclusively include $CaCO_3$, Ni/Al, sodium borohydride and reduced metal salts of Pt, Pd and Ni. The preferred solvent is ethanol and is present in an amount of from about 3 to about 5 parts by weight of the 3,5-dimethyl-4-acetoxyacetophenone. The reaction proceeds at a preferred temperature of from about 25° C. to about 40° C., a preferred hydrogen gas pressure of from about 215 to about 250 mm Hg psig. The reaction is conducted for from about 1 to about 5 hours. The resultant product is 1-(3',5'-dimethyl-4'-acetoxyphenyl)ethanol and has the appearance of a colorless oil after filtering off the catalyst and evaporating the solvent This oil is then dehydrated. Dehydration is preferably conducted by vacuum heating the oil in the presence of a polymerization inhibitor and a dehydrating agent. In one preferred embodiment, the 1-(3',5'-dimethyl-4'-acetoxyphenyl)ethanol is mixed with a $KHSO_4$ dehydrating agent and a t-butyl catechol polymerization inhibitor. Other useful dehydrating agents non-exclusively include bases, $CuSO_4$, $CuCl_2$, $Mg(ClO_4)_2$ and aluminum oxide. Other polymerization inhibitors non-exclusively include hydroquinone, tetrachloroquinone and di-t-butyl-p-cresol. The dehydrating agent is present in an amount of from about 0.25 to about 5.0 percent weight of the oil. The polymerization inhibitor is preferably present in an amount of from about 0.01% to about 5% based on the weight of the oil. The reaction vessel is heated to from about 160° C. to about 210° C., preferably 185° C. to about 190° C. at a pressure of from about 1.0 to about 15 mm Hg, preferably 1.5 to 2.0 mm Hg. The product is then distilled to a colorless liquid and then redistilled after the insertion of additional polymerization inhibitor. When the hydroxy rather than the acetoxy compound is desired, the protective group may then be split off to form the substituted 4-hydroxystyrene analogs. Hydrolysis can be carried out by either the acid or the basic method. Candidates for hydrolysis agents are $NH_3$, NaOH, KOH, and tetramethylammonium hydroxide as well as HCl or $H_2SO_4$. During hydrolysis, particularly acid hydrolysis, care must be taken that the styrene derivatives do not polymerize. A particular hydrolysis method which prevents polymerization begins with hydrazinolysis with hydrazine hydrate, and is completed by hydrolysis with acids, in particular with HCl. This method is particularly preferred.

The following non-limiting examples serve to illustrate the invention.

EXAMPLE 1

3,5-Dimethyl-4-acetoxystyrene (36.6 g, 0.30 mol) of 2,6-dimethylphenol are mixed in an Hastelloy C autoclave with 0.315 mol of acetic anhydride and 9 mols of hydrogen fluoride. The temperature is raised to 50° C. and the reaction runs for 3 hours. After extraction and wash, 47.4 g of a gray to purple solid mass of 3,5-dimethyl-4-hydroxyacetophenone is obtained. This solid is then esterified by refluxing with 4 mols of acetic anhydride for 19 hours. After removal of acetic acid and acetic anhydride by vacuum distillation the 3,5-dimethyl-4-acetoxyacetophenone is flash distilled to yield 47.7 g of a slightly yellow liquid. 0.1 mol of the 3,5-dimethyl-4-acetoxyacetophenone, 1.2 g of 5% Pd/C as catalyst and 100 ml ethanol are mixed in an autoclave and the autoclave is charged with hydrogen gas at a pressure of 215-220 mm Hg PSIG and the reaction is run for about 2 ½ hours at a temperature of about 25°-30° C. Additional catalyst is added as needed. The catalyst is then removed and the ethanol evaporated to yield 21.5 g of a colorless oil which is 1-(3',5'-dimethyl-4'-acetoxyphenyl)ethanol. 0.168 mol of 1-(3',5'-dimethyl-4'-acetoxyphenyl)ethanol is added to a flask with 0.35 g $KHSO_4$ and 0.5 g t-butyl catechol. The flask is heated to 185° to 190° C. at 1.5 to 2.0 mm Hg. A colorless liquid is distilled. After the addition of 0.15 g of t-butyl catechol, and redistillation, 26.1 g of 3,5-dimethyl-4-acetoxystyrene monomer is produced. The compound has a boiling point of 90°-91° C. at 0.5 mm of Hg and the yield is 81.8%.

EXAMPLE 2

3,5-Dibromo-4-acetoxyacetophenone.

15.7 g (0.2 mole) Acetylchloride is added dropwise to a stirred mixture of 57.1 g (0.194 mole) 3,5-dibromo-4-hydroxyacetophenone, 1.67 g 4-dimethylaminopyridine, and 19.6 g triethylamine in toluene at 60° C. After four hours of further reaction under the given conditions, the hydrochloride precipitated from the solution is filtered off and the toluene solvent is distilled from the remaining solution under vacuum and the remaining product is recrystallized from a mixture of diisopropyl ether and activated charcoal. A yield of 93% may be achieved. The white, isolated crystals have a melting point of 114° C.

EXAMPLE 3

1-(3',5'-Dibromo-4,-acetoxyphenyl)ethanol 5 g of sodium borohydride is added in small portions to an ice-cooled solution of 84 g (0.25 mole) 3,5-dibromo-4-acetoxyacetophenone in tetrahydrofuran and water. The reaction is exothermic. When all the sodium borohydride has been added and after a further 30 minutes of stirring, the reaction mixture is nearly clear. The solution is brought to a pH of 2 with 2 g hydrochloric acid, the solution is extracted twice with ether, and the combined organic phases are rinsed twice with water. After drying the ether solution, the solution is concentrated under vacuum. A yellow oil is produced, which in a high vacuum has a boiling point of 132°–139° C. at 0.002 Torr (mbar). The yield of this reaction stage after distillation is 80 g of a colorless oil.

EXAMPLE 4

3,5-Dibromo-4-acetoxystyrene

A mixture of 67.6 g (0.02 mole) 1-(3',5'-dibromo-4'-acetoxyphenyl)ethanol, 0.35 g freshly melted and then finely pulverized potassium hydrogen sulfate, and 0.5 g t-butylhydroquinone are heated at 20 Torr to 170°–190° C. The resulting product is distilled off (under vacuum) at a temperature of 140° to 160° C. It is taken up in ether, the ether solution is washed with Na2CO3, dried, and concentrated under vacuum. The remaining product is distilled at 0.02 mbar; the boiling point is 116° C. The isolated product, which is a highly viscous oil or a white, waxy solid, has a melting point of approximately 75° C. The reaction yield is 27 g.

EXAMPLE 5

Preparation of 3,5-Dibromo-4-hydroxystyrene 10 g of 4-acetoxy-3,5-dibromostyrene are dissolved in 50 ml THF and 25 ml methanol, 12 g hydrazine hydrate (80% aqueous solution) is added, and the cloudy mixture is then converted into a clear solution by adding 3 ml of water. After 40 minutes it is acidified with a semi-concentrated HCl to pH 2 and extracted twice with ether, the ether phase is washed twice with water and dried over sodium sulfate, and the ether is removed with a rotary evaporator at room temperature under aspirator vacuum. 8.5 g of crude product remain, from which 6.45 g of white crystals (mp 74° C.) are obtained by recrystallization from petroleum ether.

EXAMPLE 6 o-Cresyl Acetate

First 235.5 g (3.3 moles) acetyl chloride then 282.8 g (2.8 moles) triethylamine are added dropwise to a mixture of 324 g (3 moles) o-cresol and 36.6 g (0.3 mole) 4-dimethylaminopyridine in 1 liter of toluene. The mixture is then heated for 3 h at 65° C. The resulting solid hydrochloride is separated by filtration and the organic phase is washed twice with 1 N hydrochloric acid then with water. The solution is dried and then the solvent is recovered under vacuum. The remaining oil is distilled under vacuum. It has a boiling point of 87° C. at 12 Torr. The yield is 428.8 g.

EXAMPLE 7

4-Hydroxy-5-methylacetophenone

A total of 360 g dry $AlCl_3$ is added to a mixture of 300 g (2 moles) o-cresyl acetate and 1.2 liters nitrobenzene in small portions. The reddish mixture is kept at room temperature with moisture excluded for 12 h, and the mixture increasingly takes on a dark-green color. When the reaction mixture is poured into ice water, a light yellow emulsion is obtained, to which the quantity of a 10% hydrochloric acid needed to make it clear is added. After 1 liter of ether has been added, two phases form, from which the ether phase is separated and washed with a 7.5% potassium hydroxide solution. The aqueous phase is combined with the potassium hydroxide solution, acidified, and the resulting product, after extraction with ether, drying, and recrystallization from diisopropyl ether, is isolated. The light-brown product has a melting point of 108° to 109° C. The reaction yield is 122.8 g.

EXAMPLE 8

3-Bromo-4-hydroxy-5-methylacetophenone 110 g (0.73 mole) 4-hydroxy-5-methylacetophenone is suspended in a mixture of 370 ml acetic acid (glacial) and 370 ml H2O, the mixture is cooled to 5° C., and a solution of 116.8 g or 38 ml (0.73 mole) bromine in 100 ml acetic acid is added dropwise while cooling such that the temperature does not rise above 10° C. Addition of bromine takes about 1 h. After cooling for a further 2 h at room temperature, the product is filtered off, dried, and recrystallized from acetonitrile. 150 g of product with a melting point of 145°–146° C. can be isolated.

EXAMPLE 9

3-Bromo-4-acetoxy-5-methylacetophenone 52 g or 47 ml (0.66 mole) acetyl chloride are added dropwise to a solution of 140 g (0.6 mole) 3-bromo-4-hydroxy-5-methylacetophenone, 7.4 g 4-dimethylaminopyridine and 60.6 g (0.6 mole) triethylamine in 500 ml toluene. The resulting reaction mixture is stirred for another 3 h at 65° C. The hydrochloride formed is filtered off and the toluene phase is washed twice with 2 N hydrochloric acid then twice with water. After drying and distillation of the solvent under vacuum, 99 g of pure product is isolated. The white crystals have a melting point of 78°–80° C.

EXAMPLE 10

1-(3'-Bromo-4'-acetoxy-5'-methylphenyl)ethanol 99 g (0.37 mole) of 3-bromo-4-acetoxy-5-methylacetophenone is added to 250 ml of tetrahydrofuran and cooled to 0° C. 20 ml water is added and then 7 g (0.185 mole) sodium borohydride is added while cooling in portions such that the temperature does not exceed 20° C. After two hours stirring at room temperature, the reaction mixture is added to a mixture consisting of 100 ml concentrated hydrochloric acid, 200 ml water, and 250 g ice, the mixture is thoroughly stirred, and then extracted with ether. The ether phase is washed first with a 5% sodium carbonate solution then with water. After distilling the solvent, 96.3 g of a viscous oil is obtained as the crude product which is then distilled under vacuum according to Example 3 and yields 86.8 g of product.

EXAMPLE 11

3-Bromo-4-acetoxy-5-methylstyrene

A mixture of 28 g 1-(3'-bromo-4'-acetoxy-5'-methylphenyl)ethanol and 0.5 g freshly prepared potassium hydrogen sulfate is heated under a 20 Torr vacuum to 190°-200° C. The distillate is transferred to an ice-filled reaction vessel which contains 2 g t-butylhydroquinone. After 2 h, the distillate is taken up in ether, the ether phases are treated with a 5% sodium carbonate solution and dried, then the solvent is distilled off under vacuum. At 0.05 Torr, 6.8 g of an impure product is obtained at a temperature of 86° to 89° C., from which 18 g of pure monomer can be obtained.

EXAMPLE 12 (COMPARATIVE EXAMPLE)

Attempted direct reduction of 3,5-dibromo-4-hydroxyacetophenone 10 g of 3,5-dibromo-4-hydroxyacetophenone are dissolved in methanol, cooled to 0° C., at which point the calculated amount of sodium boron hydride is slowly added with stirring. After one minute, thin layer chromatography shows the presence of 4-ethylphenol, but not of 1-(3',5'-dibromo-4'-hydroxyphenyl)ethanol (by comparison with authentic samples). After one hour, the mixture is worked up by pouring into water, extracting the ether, and drying on a rotary evaporator. Analysis of the products by NMR spectroscopy shows the material to be a mixture of starting material and 4-ethylphenol, with no alcohol reduction product present. Similar results are obtained with other solvents and complex hydrides as well as with attempted catalytic hydrogenations.

EXAMPLE 13

Dehydration of 1-(3',5'-dibromo-4'-acetoxyphenyl)ethanol with copper(II)sulfate:

5 g 1-(3',5'-dibromo-4-acetoxyphenyl)ethanol are dissolved in 50 g of toluene, to which mixture are added 0.25 g of anhydrous copper(II)sulfate. The mixture is refluxed for 2 hours and the toluene then removed on a rotary evaporator. A yellow oil remains which after recrystallization from petrol ether yields 2.9 g of 3,5-dibromo-4-hydroxystyrene as white crystals, mp. 75° C.

What is claimed is:

1. A process for the production of 3,5-disubstituted-4-acetoxystyrene which comprises (a) acylating 2,6- disubstituted phenol under suitable catalysis to provide 3,5-disubstituted-4-hydroxyacetophenone, then (b) esterifying the 3,5-disubstituted-4-hydroxyacetophenone to produce 3,5-disubstituted-4-acetoxyacetophenone, then (c) hydrogenating the 3,5-disubstituted-4-acetoxyacetophenone to form 1-(3',5'-disubstituted-4'-acetoxyphenyl)ethanol and then (d) dehydrating the 1-(3',5'-disubstituted-4'-acetoxyphenyl)ethanol to form 3,5-disubstituted-4-acetoxystyrene, wherein each of said 3,5-substitutions are independently $C_1$ to $C_{10}$ alkyl or alkoxy, amino or halogen.

2. The process of claim 1 wherein step (a) is conducted by a Fries rearrangement process.

3. The process of claim 1 wherein step (a) is conducted by a Friedel-Crafts acylation process.

4. The process of claim 1 wherein step (a) is conducted with a hydrogen fluoride catalyst.

* * * * *